United States Patent [19]

Tmenov et al.

[11] 4,229,604
[45] Oct. 21, 1980

[54] PROCESS FOR PRODUCING UNSATURATED HYDROCARBONS

[76] Inventors: Dzantemir N. Tmenov, Prazhskaya ulitsa, 3, kv. 222; Nikolai I. Svintsov, ulitsa Vernadskogo, 63, kv. 38; Lidia P. Shapovalova, Kharkovskoe shosse, 12, kv. 43; Albert V. Tabakov, ulitsa Boichenko, 17, kv. 38; Mikhail L. Dvoretsky, ulitsa Bereznyakovskaya, 26, kv. 64, all of Kiev; Gavril I. Vasiliev, ulitsa Kommunisticheskaya, 38, kv. 40; Gennady P. Zhestovsky, ulitsa Chernyshevskogo, 27, kv. 15, both of Novokuibyshevsk Kuibyshevskoi oblasti; Valentina D. Kandalova, Pervomaiskaya ulitsa, 51/23, kv. 33, Moscow; Boris S. Korotkevich, Fortunatovskaya ulitsa, 31/35, kv. 71, Moscow; Anatoly I. Lukashov, Palekhskaya ulitsa, 9, korpus 1, kv. 65, Moscow; Valery P. Lukyanenko, Garmotnaya ulitsa, 22, kv. 20; Roman I. Polataiko, Volgogradskaya ulitsa, 39, kv. 96, both of Kiev; Evgeny A. Malov, ulitsa Repina, 1, kv. 18, Novokuibyshevsk Kuibyshevskoi oblasti; Jury A. Shmuk, Leninsky prospekt, 13, kv. 3, Moscow, all of U.S.S.R.

[21] Appl. No.: 9,522

[22] Filed: Feb. 5, 1979

[51] Int. Cl.$^2$ .................... C07C 15/10; B01J 23/84; B01J 29/16
[52] U.S. Cl. .................... 585/445; 252/457; 252/468; 585/624; 585/628; 585/658
[58] Field of Search ............... 585/445, 624, 628, 658; 252/457, 468

[56] References Cited

U.S. PATENT DOCUMENTS

| | | | |
|---|---|---|---|
| 2,376,549 | 5/1945 | Mavity | 585/445 X |
| 2,547,380 | 4/1951 | Fleck | 208/243 X |
| 3,488,402 | 1/1970 | Michaels et al. | 585/628 X |
| 3,577,477 | 5/1971 | Boutry et al. | 585/624 |
| 3,862,256 | 1/1975 | Isailingold et al. | 585/626 |
| 3,969,428 | 7/1976 | Ishikawa et al. | 252/468 |
| 4,140,626 | 2/1979 | Bertolacini et al. | 208/216 R |

Primary Examiner—Herbert Levine
Assistant Examiner—G. E. Schmitkons
Attorney, Agent, or Firm—Lackenbach, Lilling & Siegel

[57] ABSTRACT

A process for producing unsaturated hydrocarbons which comprises contacting a paraffin, monoolefin and/or alkylaromatic compounds with a catalyst at a temperature within the range of from 400° to 700° C. in the presence of an inert gas and/or steam. The catalyst comprises a carrier having deposited thereonto an oxide of molybdenum in an amount of from 5 to 35% by weight of the catalyst. As the carrier, use is made of a granulated porous crystalline silica modified with magnesia in an amount of from 1 to 20% by weight of the carrier; a granulated magnesium-titanium carrier consisting of 50 to 95% by weight of MgO and 50 to 5% by weight of TiO$_2$, or a granulated magnesium-aluminum carrier consisting of 70 to 95% by weight of MgO and 5 to 30% by weight of Al$_2$O$_3$. Through the spent catalyst an oxygen-containing gas is passed at a temperature within the range of from 400° to 700° until catalytic activity is restored to the catalyst.

The process, according to the present invention, ensures a high selectivity; substantially simplifies temperature control in the reaction zone; avoids the possibility of forming of a hazardous mixture of hydrocarbons with oxygen; and simplifies purification of waste waters.

9 Claims, No Drawings

PROCESS FOR PRODUCING UNSATURATED HYDROCARBONS

FIELD OF THE INVENTION

The present invention relates to the production of unsaturated hydrocarbons.

Said unsaturated hydrocarbons such as butylenes, isoamylenes, divinyl, isoprene, styrene, vinyltoluene are valuable monomers for the manufacture of various types of synthetic rubber, plastics, elastomers as well as for the starting products of basic organic synthesis.

BACKGROUND OF THE INVENTION

Known in the art are various processes for the production of unsaturated hydrocarbons.

Thus, known is a process for the production of unsaturated hydrocarbons from saturated ones at a temperature within the range of from 400° to 800° C. in the presence of gaseous oxygen and a catalyst containing molybdenum as well as nickel or cobalt. The yield of butadiene produced by this process does not exceed 10.1% with the selectivity relative thereto of 31.0% and relative to the total butylenes-butadiene of 46.4%.

Also known in the art is a process for producing mono- and di-olefins by an oxidizing dehydrogenation of paraffins at a temperature within the range of from 400° to 700° C. in the presence of gaseous oxygen and a catalyst consisting of oxides of molybdenum and/or tungsten and at least one of the following metals: chromium, manganese, iron, nickel and cadmium. In accordance with this process, the yield of butadiene from n-butane does not exceed 21.6% with a selectivity relative thereto of 53.6% and relative to the total butylenes-butadiene of 64.8%.

A principal disadvantage of the above-discussed prior art processes resides in low conversion of dehydrogenated hydrocarbons and insufficient selectivity relative to the desired products.

The closest analogue of the process according to the present invention is a process for producing mono- and diolefins by an oxidizing dehydrogenation of, e.g. paraffin hydrocarbons, at a temperature within the range of from 400° to 700° C. and the molar ratio of oxygen to the paraffin hydrocarbon of from 0.1 to 3.0:1 in the presence of an inert vehicle such as argon, nitrogen, helium, steam or mixtures thereof.

The process is conducted on a catalyst comprising oxides of, e.g., molybdenum and magnesium, with additives of cobalt, iron, chromium, vanadium, nickel, silicon, tin, boron, bismuth, titanium, niobium, gadolinium, dysprosium, gallium and zirconium. The yield of butadiene from n-butane by this process is 36.6% with a selectivity relative thereto of 54.7% and relative to the total butylenes-butadiene of 64.3%.

For increasing the mechanical strength of the catalyst, the active component is applied on a carrier, such as alumosilicate, aluminum oxide, silica gel. However, the use of such catalysts, e.g. with the application of alumosilicate, in accordance with the above-cited method, leads to lowering of the butadiene yield from n-butane to 4.7% with the selectivity reduced to 14.3%. Thus, the method is characterized by low selectivity, and, in the case of using a catalyst with a carrier, by a low yield of the desired dehydrogenation products.

SUMMARY OF THE INVENTION

It is an object of the present invention to provide a process for producing unsaturated hydrocarbons which makes it possible to increase the yield of the desired products and increase selectivity of the process.

This and other objects of the present invention are accomplished in a process for producing unsaturated hydrocarbons by contacting paraffin, mono-olefin and/or aromatic compounds having catalyst comprising a carrier with a deposited thereonto an oxide of molybdenum in an amount of from 5 to 35% by weight of the catalyst in the presence of an inert gas and/or steam at a temperature within the range of from 400° to 700° C. In accordance with the present invention, the catalyst carrier is made of a granulated porous crystalline silica modified by magnesia in an amount of from 1 to 20% by weight of the carrier, a granulated magnesium-titanium carrier consisting of 50 to 95% by weight of MgO, and 50 to 5% by weight of $TiO_2$, or a granulated magnesium-aluminum carrier consisting of 70 to 95% by weight of MgO and 5 to 30% by weight of $Al_2O_3$. At a temperature within the range of from 400° to 700° C. an oxygen-containing gas is passed through the spent catalyst until regeneration of the catalytic activity of the catalyst occurs.

As the starting material use may be made of various organic compounds, namely olefins, paraffins and alkylaromatic hydrocarbons. In the case of using paraffins along with dienes there is formed a certain amount of monoolefins which together with the unreacted starting material are recycled back into the reaction zone to increase the yield of diene hydrocarbons.

Selectivity of the process is increased by diluting the starting hydrocarbons with inert diluents, namely nitrogen, argon, steam and the like. The molar ratio between the hydrocarbon and the diluent is varied within a wide range of from 1:3 to 1:30.

Vapors of the starting feed (butane, butylenes, isopentane, isoamylenes, ethylbenzene, ethyltoluene and the like) in a mixture with a diluent are contacted with the catalyst at a temperature within the range of from 400° to 700° C. (preferably from 450° to 650° C.). As a result, a process of dehydrogenation of the starting organic compounds occurs, wherein the hydrogen of said compounds combines with the oxygen of the catalyst to form water. The content of oxygen in the catalyst is lowered. This results in a decrease of the valency of molybdenum. Reduction of the catalyst is accompanied by a decrease of its activity and substantial loss of activity of the feed conversion. Therewith, selectivity of the catalyst action is retained at the initial level or even increased.

To maintain high activity of the catalyst, periodic oxidizing regeneration of the catalyst is performed by means of an oxygen-containing gas such as air at a temperature within the range of from 400° to 700° C. Upon oxidizing regeneration there occurs elimination of carbonaceous deposits from the catalyst surface and oxidation of the catalyst to its original state. After discontinuation of each stage of the dehydrogenation and regeneration process, the catalyst is purged with a stream of an inert gas. Therefore, in accordance with the present invention, there is no contact of the hydrocarbon with oxygen in the gas phase which increases selectivity of the process and elevates the yield of the desired products due to the diminished role of the reactions of deep and partial oxidation and oxidizing cracking of hydrocarbons.

The catalyst according to the present invention, as has been already mentioned hereinbefore, comprises a carrier having deposited thereonto an oxide of molybdenum. In the catalyst containing, as the carrier, a granulated crystalline silica modified with magnesia, high mechanical strength of the catalyst is ensured on account of a rigid crystal lattice of silica, while the presence of magnesia at its surface results in the formation of an active magnesium molybdate and a substantial (by 10 to 40 times) increase of the specific surface area of the catalyst.

The granulated small-size carrier used in the process according to the present invention comprises a mixture of magnesia with titanium dioxide or alumina. An increased content of magnesia in the carrier composition up to 50 to 95% by weight contributes to an increased yield of the desired products and higher selectivity of the dehydrogenation process. The presence of titanium dioxide or alumina increases the mechanical strength of the carrier and makes it possible to lower the calcination temperature during its preparation.

The process of dehydrogenation of hydrocarbons may also be conducted on catalysts whose active phase contains, in addition to oxides of molybdenum, oxides of cobalt, nickel, iron or manganese in an amount of from 3.7 to 15% by weight of the catalyst. Such catalysts have different structural modifications. The catalyst type affects selectivity of the process of dehydrogenation of particular hydrocarbons.

The catalyst is employed in the shape of tablets, noodles, rings and granules of various dimensions, preferably of from 0.01 tp 15.00 mm.

In order to prolong the service life of the catalyst which is essential for a dehydrogenation process performed in a stationary and liquified bed of the catalyst, into the dehydrogenation zone there is added a small amount of oxygen (up to 0.1 mole per mole of the starting hydrocarbon feed). This is of great importance, since the operation time of the catalyst (duration of dehydrogenation) in an apparatus with a stationary bed or in reactors with a fludized bed usually exceeds 3 to 5 minutes. The use of small amounts of oxygen in the dehydrogenation zone does not substantially affect the yield of the desired products and selectivity of dehydrogenation.

In accordance with the present invention, the catalyst employed in the process for producing unsaturated hydrocarbons is prepared by impregnation of the abovementioned carriers with an aqueous solution of ammonium molybdate to yield a suspension. From the resulting suspension water is removed by evaporation. After evaporation, the thus-obtained mass is subjected to calcination at a temperature within the range of from 350° to 700° C. The calcination is effected in an inert or oxidizing medium.

During the impregnation of the carrier with an aqueous solution of ammonium molybdate, filling of the carrier pores with this solution occurs. In the subsequent treatment operations (evaporation, calcination) forming of a catalyst occurs as a result of the removal of water and decomposition of ammonium molybdate.

To intensify the process of dehydration of the suspension, it is advisable to carry out the evaporation under vacuum.

In some cases in the calcination process, sintering of particles is possible at a rapid increase in temperature which results in variations of the fraction composition of the catalyst and this, in turn, necessitates inclusion of additional stages such as crushing, and separation. To avoid this, calcination of the resulting mass should be preferably carried out in a suspended bed.

In order to increase activity and selectivity of the catalyst, it is advisable to include in its composition oxides of cobalt, iron, nickel or manganese in an amount of from 3.7 to 15% by weight of the catalyst. To this end, prior to calcination, the carrier is also impregnated with an aqueous solution of cobalt nitrate, or a nitrate of nickel, iron or manganese. This impregnation and the impregnation with an aqueous solution of ammonium molybdate are conducted in any sequence. In between the respective impregnations water is removed from the resulting suspension by evaporation.

In order to further increase activity and selectivity of the catalyst, it is advisable to repeatedly and alternatively (up to 3-12 times) perform impregnation of the carrier with a solution of said salts including ammonium molybdate, followed by evaporation of water from the suspension. Thereafter calcination of the resulting mass is carried out at a temperature of from 350° to 700° C. This ensures a more uniform distribution of the active phase within the volume of the catalyst granules and an increase in fineness of the active component at the surface of the porous carrier.

Increased fineness of the active component is associated with the growth of its surface area accessibility to the reagents which, in turn, makes it possible to perform the dehydrogenation process at a higher rate at the same charge of the catalyst. Uniformity of distribution of the active component within the volume of the catalyst granules prevents a rapid loss of the catalyst activity during the operation.

A further increase of the catalyst activity and simplification of the technology of its preparation is ensured by treating the resulting mass, i.e. the carrier, already impregnated with aqueous solutions of ammonium molybdate and a nitric acid salt and dried, prior to the calcination is treated with an aqueous solution of ammonia, amines or aminoalcohols followed by the removal of water by evaporation.

To this end, use may be made of methyl- and triethylamines, mono-, di- and triethanolamines and the like. The treatment therewith makes it possible to achieve a uniform distribution of active components within the volume of the catalyst granules and exclude repeated operations in the preparation of a polycomponent catalyst.

The use in the process according to the present invention of the principle of alternative contacting of the hydrocarbons fed to hydrogenation and oxygen supplied to regeneration of the spent catalyst makes it possible to increase the process selectivity as compared to the prior art processes (cf. U.S. Pat. No. 3,862,256). Thus, upon dehydrogenation of n-butane according to the process of the present invention, selectivity relative to butadiene is 75.1% as compared to 54% in the prior art process, while selectivity relative to the total of butylenes-butadiene constitutes 85.4% as compared with 64.3% in the prior art process.

This relatively low selectivity in the production of unsaturated hydrocarbons by the known method is apparently due to intensive side reactions of a deep and partial oxidation of hydrocarbons in the presence of gaseous oxygen supplied into the dehydrogenation zone along with the starting feed. A similar decrease in selectivity relative to dehydrogenation products under the conditions of simultaneous supply of hydrocarbons and air oxygen onto the catalyst has been observed in our case too. Thus, when the process is carried out in the absence of gaseous oxygen in the reaction zone, the yield of butadiene from n-butane is 27%, the yield of combustion products (CO and $CO_2$) is 8.6%. Upon addition of oxygen into the starting feed composition at the stage of dehydrogenation only in the amount of 0.5 mole per mole of n-butane, the yield of butadiene is reduced to 22.2%, while the yield of combustion products is increased to 20.2%, whereas total selectivity relative to the whole dehydrogenation products ($C_4H_8$-$C_4H_6$) is reduced from 75.0 to 54.1%. The yield of the products of partial oxydation of hydrocarbons, i.e. furan and other oxygen-containing compounds, in this case is increased by about 5 times.

Furthermore, carrying out the process in the absence of oxygen facilitates temperature control in the reaction zone (owing to lowered intensity of highly exothermal combustion reactions). There is totally avoided the possibility of forming a hazardous mixture of hydrocarbons with oxygen. Also, the problem of purification of waste waters due to a lowered yield of oxygen-containing products of a partial oxidation of hydrocarbons is substantially simplified.

Due to the fact that the stock of oxygen in the catalyst is limited, the period of its effective operation under the conditions of dehydrogenation is not long. This is a substantial obstacle to practical implementation of the process. To avoid this, it is advisable to conduct dehydrogenation following the process according to the present invention, i.e. with continuous displacement of the spent catalyst from the dehydrogenation zone to the regeneration zone, with subsequent recycle of the catalyst back to the dehydrogenation zone after restoration of its activity. This displacement of the catalyst and its operation in a suspended bed imposes increased requirements on the mechanical strength and wear-resistance of the catalyst and makes the use of catalysts prepared by the prior art methods without a carrier practically impossible.

At the same time, the use of catalysts prepared by the prior art method with a carrier leads to a sharp reduction of the yield of the desired products of dehydrogenation of hydrocarbons.

The catalyst as employed in the process according to the present invention, allows the desired product to be obtained in a high yield. Moreover, this catalyst, owing to a mechanically durable porous carrier features a high wear-resistance and ability to retain its fractional composition which enables its use in apparatus with both stationary and mobile or liquified catalyst beds.

The porous crystalline silica as used as carrier for the catalyst in the process according to the present invention has a small specific surface area (within the range of from 0.15 to 2 $m^2/g$) and a low absorption power relative to the active components of the catalyst. Modification thereof with magnesia makes it possible to increase the specific surface area of the carrier up to 10–12 $m^2/g$. Magnesia, while reacting during its application with the solution of ammonium molybdate, forms a magnesium molybdate which is catalytically active in the dehydrogenation reaction, and in the preparation of, for example, a cobalt-molybdenum catalyst, it stabilizes the active a-phase of cobalt molybdate.

In the process according to the present invention use may be also made of a catalyst having, as its carrier, a molded and calcined mixture of finely divided magnesia and titania or alumina. In this case magnesia forms a matrix of the carrier granule, while the titania or alumina incorporated therein substantially lowers the calcination temperature of granules and makes it possible to obtain the carrier with a sufficiently developed specific surface area, since the specific area of magnesia is considerably reduced with the growth of calcination temperature.

The catalysts used in the process according to the present invention possess high catalytic activity and selectivity, thermal stability, impact resistance and ability to withstand considerable temperature gradients. Thus, wear of a small-size cobalt-molybdenum catalyst based on magnesium-titanium carrier constitutes 3–4%, while the standard crushed glass-like alumosilicate under the same conditions has a wear of 18–20% by weight. Still higher wear-resistance is characteristic of catalysts based on a porous crystalline silica (quartz). Therefore, the catalysts according to the present invention are highly effective in a dehydrogenation process in reactors of all the above-mentioned types.

DETAILED DECRIPTION OF THE INVENTION

The process according to the present invention is technologically simple and may be performed in the following manner.

According to the present invention, production of unsaturated hydrocarbons by way of dehydrogenation of paraffinic, monoolefin and/or alkylaromatic compounds is effected by contacting their vapors with the above-described catalyst at a temperature within the range of from 400° to 700° C. in apparatus of different design. In order to increase selectivity of dehydrogenation, the feed vapors are diluted with steam and/or an inert gas such as nitrogen, argon, helium. In the periodic scheme of operation, into an apparatus with a stationary bed of a granulated catalyst or with a liquified bed of a small-size catalyst the starting hydrocarbon feed is supplied along with the diluent at the above-mentioned temperature. Contact time of the gas stream and the catalyst is varied within the range of from 0.01 to 100 min. The reaction products are cooled and after separation of the diluent are delivered to the fractionation system. Duration of passing the feed through the apparatus ranges from 15 sec to 20 min. After discontinuation of the feed supply, the apparatus is purged with an inert gas to remove vapors of hydrocarbons. The spent catalyst is then regenerated at a temperature within the range of from 400° to 700° C. for a period of from 15 seconds to 20 minutes. The regeneration is effected in a current of an oxygen-containing gas such as air until restoration of the catalyst activity. To remove oxygen from the apparatus after discontinuation of the regeneration, the catalyst is purged with steam or an inert gas and feed is again admitted into the apparatus for the following cycle.

To prolong the service life of the catalyst under the conditions of dehydrogenation, it is possible to introduce, simultaneously with the feed, a small amount of oxygen (not more than 0.1 mole per one mole of the starting hydrocarbon feed).

Continuous operation is obtained as a result of combination, in one plant, of two or more reactors, wherein the stages of dehydrogenation, purging and regeneration are time-shifted.

It is most advisable to perform the process according to the present invention in systems with transportation of the catalyst, for example in a system of two fluidized bed apparatus with a small-size catalyst. In the first apparatus dehydrogenation is effected under the above-described conditions. The spent catalyst via a transportation line is continuously fed to the oxidizing regeneration into the second apparatus (regenerator). The regenerated catalyst is recycled back to the dehydrogenation zone. During transportation of the catalyst, it is subjected to purging for the removal of hydrocarbons and oxygen. Apparatus dimensions, the catalyst level therein, circulation ratio of the catalyst are determined by the plant capacity, composition of the catalyst and an optimal degree of the catalyst oxidation.

However, taking into account the fact that in many cases the catalyst possesses the highest selectivity and activity only within very short periods of time and it is economically efficient to use a catalyst with a lowered content of active components capable of carrying small amounts of oxygen, the most suitable for commercial implementation is the following technological embodiment of the process according to the present invention.

Heated hydrocarbon feed vapors along with said diluents are supplied into the bottom section of a lift-reactor, whereinto through special means of the injector type a small-size catalyst is fed from the regenerator. The catalyst is conveyed by the stream of feed, diluent and the reaction products and separated therefrom in a separator means. The reaction products are further purified to remove the entrained catalyst particles, whereafter they are cooled, separated from the diluent and further delivered to the separation system, wherefrom the unreacted feed and intermediate reaction products are recycled to the reactor.

The catalyst, after purging-off the hydrocarbons, is passed from the separator, cyclones and filters to the regenerator unit with a fluidized bed of the catalyst, whereinto an oxygen-containing gas, e.g. air, is fed too. After another purging, the regenerated catalyst is recycled into the bottom part of the reactor. For plants with a higher capacity, it is possible to combine in one system several lift-reactors with a common regenerator and a common system of separation of the reaction products.

The time of contact of the feed and the catalyst is varied within the range of from 0.5 to 15 seconds; residence time of the catalyst in the lift-reactor and separator does not exceed 2–3 minutes.

The process of dehydrogenation according to the present invention under the above-mentioned conditions makes it possible to provide for plants with a higher unit output with a high yield of the desired products and increased selectivity relative thereto. Owing to the continuous scheme of the process and constant composition of the reaction products, separation thereof is facilitated along with reduction of losses of the products at this stage; temperature control and utilization of heat of the off-streams becomes easier.

At the same time, this mode of dehydrogenation imposes quite severe requirements on activity, selectivity and wear-resistance of the catalyst. Preparation of the catalyst employed in the process according to the present invention is effected in the following manner.

First, the carrier is prepared. To this end, 96–99% by weight of finely divided quartz sand are mixed with 1–4% by weight of bicarbonate (carbonate) of sodium, potassium or lithium, or 50–95% by weight of magnesia are mixed with 5–50% by weight of titania, or 70 to 95% by weight of magnesia are mixed with 5 to 30% by weight of alumina (aluminum hydroxide). The resulting mixture is granulated to give pellets of required dimensions and shape. The granulation is performed with the addition of water, aqueous solutions of polyvinyl alcohol, dextrin, carboxymethylcellulose using tabletting machines, extrusion-type or adhesion granulators of various designs. To prepare a small-size catalyst, spray drying is used along with adhesion-type granulators. The resulting granules are dried at a temperature within the range of from 60° to 150° C. and calcination thereof is effected at a temperature of from 900° to 1,300° C. for a period of from 30 minutes to 6 hours. The calcination duration and temperature are selected depending on the composition of the starting charge and requirements imposed on the resulting carrier.

During calcination of granules, silicates of alkali metals or titanates and aluminates of magnesium are formed which ensure durable bonding of particles of silica or magnesia in the carrier granules. At a temperature of above 800° C. a phase transition of $\beta$-quartz of crystoballite is observed.

The calcined granules of the porous quartz carrier are modified by impregnation with an aqueous solution of magnesium nitrate. The solution excess is removed by decantation or evaporation. Then the carrier is calcined at a temperature within the range of from 300° to 500° C. to decompose magnesium nitrate.

The thus-prepared carriers have high mechanical strength, and increased heat-resistance. Their abrasion resistance is higher than that of alumosilicate. The specific surface area of the carriers, depending on the composition and preparation conditions, is varied within the range of from 2 to 15 m$^2$/g, porosity is equal to 0.2–0.4 cm$^3$/cm$^3$.

The thus-prepared lot of the carrier of the required fractional composition is contacted with a concentrated solution of ammonium molybdate. To ensure a more uniform impregnation of granules, it is desirable to set the vessel with the carrier under vacuum prior to pouring the solution thereinto. Due to the interaction between ammonium molybdate and magnesia the suspension is heated-up and ammonia is liberated and evacuated from the vessel. After residence in the reactor for 0.5–5 hours, water is evaporated from the suspension at a temperature within the range of from 60° to 180° C. To avoid aggregation, the impregnation and evaporation are carried out under continuous or periodic stirring of the suspension. The vaporization process can be intensified by setting the vessel under vacuum. For this reason preparation of the catalyst should be preferably effected in hermetically sealed heated apparatus provided with a low-speed stirrer for example in Z-shaped mixers. Completion of the process is determined by a rapid increase in temperature in the apparatus.

To prepare a polycomponent catalyst by this method, the mass resulting from evaporation is contacted with an aqueous solution of cobalt, nickel, iron or manganese nitrate. Impregnation and evaporation are effected as described above.

Impregnation with evaporation makes it possible to prepare a catalyst of a predetermined composition and lower consumption of the active components.

To prepare a polycomponent catalyst with a more uniform distribution of the active phase within the volume of granules and with a better contact among the components, impregnation is effected from diluted solutions of salts alternatively, i.e. repeating operations of impregnation with each salt and a subsequent evaporation for 3 to 12 times. Thus, in the preparation of a cobalt-molybdenum catalyst, the carrier is contacted with a solution of ammonium molybdate; water is evaporated from the suspension and then contacted with a solution of cobalt nitrate and the suspension is again evaporated, whereafter impregnation with a solution of ammonium molybdate is effected and so on, the procedure is repeated for 3 to 12 times. As a result of a more uniform distribution of the active phase within the volume of granules and higher degree of fineness thereof, the catalyst activity is substantially increased, i.e. by 20 to 50%. The same effect may be achieved in the following manner. After impregnation of the carrier with a solution of ammonium molybdate, evaporation, treatment with solutions of nitrates of cobalt, nickel, iron or manganese and subsequent evaporation of water from the suspension, the resulting mass is treated with aqueous solutions of ammonia, amines or aminoalcohols. Then evaporation of water is repeated with subsequent calcination of the mass under the above-mentioned conditions. Upon treatment with ammonia, amines or aminoalcohols during the preparation of polycomponent catalysts, e.g. cobalt-molybdenum catalyst, there occurs combination of the active components to complexes containing cations $Co^{2+}$ and $Mo^{6+}$ as well as $NH_4^+$ and $OH^-$ groups which ensures a more uniform distribution of the components of the active phase and increases its fineness. For this reason, in such catalysts no free oxides of molybdenum and cobalt are found (i.e. the process of the preparation of the catalyst goes to its completion).

All other conditions being equal, the yield of divinyl and selectivity on a treated catalyst, during its preparation, with monoethanolamine is about 2 times as high as that of a similar catalyst prepared by a single-application method.

In accordance with the process of the present invention after application of the active components and evaporation of water, the dried mass is calcined for the final formation of the catalyst for 0.5 to 25 hours (preferably from 2 to 6 hours) at a temperature within the range of from 350° to 700° C. (preferably from 450° to 600° C.). To avoid reduction of the catalyst, calcination is conducted in an inert or oxidizing medium. To prevent variations of the fractional composition of the small-size catalyst due to sintering of its particles, it is advisable to perform calcination of said catalyst in a fluidized bed in a current of an inert of an oxygen-containing gas.

For a better understanding of the present invention some specific examples illustrating the process for producing unsaturated hydrocarbons are given hereinbelow.

EXAMPLE 1

A carrier is prepared in the following manner. 95% by weight of magnesia are mixed with 5% by weight of titania. The resulting mixture is plastified by adding a 2% solution of polyvinyl alcohol and by the rubbing method granules of a size of from 0.1 to 0.3 mm are prepared. The granules are dried for two hours at a temperature within the range of from 80° to 90° C. and calcined in a muffle furnace for one hour at the temperature of 650° C.

To prepare the catalyst, there are mixed a solution of 24.3 g of ammonium molybdate in 100 ml of distilled water and 70.0 g of the carrier prepared as above (impregnation). As a result, there is obtained a suspension, wherefrom water is removed by evaporation with a progressive increase in temperature up to 150° C. The resulting mass is subjected to calcination in a current of air at a temperature of from 590° to 600° C. for 25 hours. A catalyst is thus produced having the following composition: $MoO_3$ 22% by weight, MgO 74.1% by weight, $TiO_2$ 3.9% by weight. Specific surface area of the catalyst is 65 $m^2/g$.

Into a reactor with a fluidized bed of the thus-prepared catalyst (fraction with a particle size of from 0.1 to 0.3 mm) at a temperature 590° C. there are alternatively fed n-butane with argon, and air. Molar ratio between n-butane and argon is equal to 1:10. Space velocity of the supply is 450 $hr^{-1}$ and the supply duration is 0.5 minutes. The total duration of the process is 35 hours.

Conversion of n-butane is 48.2%, the yield of butadiene is 36.2% with selectivity relative thereto of 75.1% and relative to the total of butylenes-butadiene 85.4%.

EXAMPLE 2

To prepare a catalyst a solution of 10.0 g of ammonium molybdate in 20 ml of distilled water is mixed with 16.0 g of the carrier prepared in the foregoing Example 1. The resulting suspension is subjected to evaporation at a temperature within the range of from 80° to 130° C. The calcination is effected at a temperature of from 680° to 700° C. in an atmosphere of nitrogen for 0.5 hour. A catalyst is thus produced and its composition is the following: $MoO_3$ 35% by weight, MgO 61.7% by weight, $TiO_2$ 3.3% by weight. Specific surface area of the catalyst is 41.3 $m^2/g$.

Into a reactor with a fluidized bed of this catalyst at a temperature of 550° C. there are alternatively fed n-butane in a mixture with argon, and air. Molar ratio between n-butane and argon is 1:13. Space velocity of the feed supply is 105 $hr^{-1}$, duration of the supply is 0.5 min. Space velocity of the air supply is 1,350 $hr^{-1}$ and duration of the supply is 0.5 min. The total duration of the process is 5 hours.

Conversion of n-butane is 30.2%, the yield of butadiene is 23.2% with selectivity relative thereto of 76.8% and relative to the total of butylenes-butadiene of 85.8%.

EXAMPLE 3

To prepare a catalyst a solution of 24.3 g of ammonium molybdate in 100 ml of distilled water is mixed with 70.0 g of a magnesium-aluminum carrier consisting of 70% by weight of magnesia and 30% by weight of alumina. (Preparation of the carrier is effected in a manner similar to that described in the foregoing Example 1). The stages of evaporation and calcination are conducted under the conditions of Example 1.

A catalyst is prepared having the following composition: $MoO_3$ 21.1% by weight, MgO 55.3% by weight, $Al_2O_3$ 23.6% by weight. Specific surface area of the catalyst is 16.3 $m^2/g$.

Into a reactor with a fluidized bed of the catalyst prepared as above at the temperature of 595° C. there are alternatively added n-butane in a mixture with steam, and air. Molar ratio between n-butane and steam is 1:30. Space velocity of the mixture supply is 40 $hr^{-1}$ and the supply duration is 0.5 min. Space velocity of the air supply is 450 $hr^{-1}$ and the supply duration is 0.5 min. The total duration of the process is 4 hours.

Conversion of n-butane is 24.0%, the yield of butadiene is 11.0% with selectivity relative thereto of 45.9% and relative to the total of butylenes-butadiene of 51.3%.

EXAMPLE 4

Use is made of the catalyst described in the foregoing Example 1. The dehydrogenation process is performed under the conditions of Example 1. As the starting feed use is made of n-butylenes (the content of n-butylenes is 99.8% by volume), and of steam as a vehicle. The total duration of the process is 38 hours.

Conversion of butylenes is 85.1%, the yield of butadiene is 79.5% with selectivity relative to butadiene of 93.5%.

EXAMPLE 5

To prepare a catalyst, use is made of 100 g of a carrier with a particle size of 0.1–0.3 mm consisting of 75% by weight of magnesia and 25% by weight of titania and calcined at the temperature of 1,000° C., a solution of 32.9 g of cobalt nitrate in 400 ml of distilled water (solution A) and a solution of 20.0 g of ammonium molybdate in 400 ml of distilled water (solution B).

Preparation of the catalyst is effected by alternative two-step application of the catalyst components (cobalt and molybdenum) according to the following scheme:

1-st step: solution A is mixed with the carrier and water is removed from the resulting suspension by evaporation at a temperature within the range of from 80° to 120° C.;

2-nd step: the mass obtained in the first stage is mixed with solution B and water is removed from the resulting suspension by evaporation at a temperature within the range of from 80° to 150° C.

The resulting mass is calcined at a temperature of 550° C. in a suspended bed in a stream of air for 5 hours.

A catalyst of the following composition is obtained: MgO 66.5% by weight, $TiO_2$ 22.2% by weight, CoO 4.0% by weight, $MoO_3$ 7.3% by weight.

Specific surface area of the catalyst is 12.3 m²/g. The dehydrogenation process on the thus-prepared catalyst is conducted under the conditions described in the foregoing Example 2.

Conversion of n-butane is 25.0%, the yield of the butadiene is 6.1% with selectivity relative thereto of 24.2% and relative to the total of butylenes-butadiene of 37.5%.

EXAMPLE 6

A catalyst is prepared following the procedure described in the foregoing Example 5, except that application of the active components (cobalt and molybdenum) is effected in 4 and 12 stages according to the following two schemes:

1-st scheme:

In the 1-st stage 200 ml of solution A are mixed with the carrier and water is removed from the resulting suspension by evaporation at a temperature within the range of from 80° to 120° C.;

In the second stage the mass resulting from the 1-st stage is mixed with 200 ml of solution B and water is removed from the resulting suspension by evaporation at a temperature of from 80° to 150° C.;

In the 3-rd stage the mass resulting from the 2-nd stage is added with the remaining portion of solution A and water is evaporated at a temperature within the range of from 80° to 120° C.;

In the 4-th stage the mass resulting from the 3-d stage is added with the remaining portion of solution B and water is removed by evaporation at a temperature of from 80° to 150° C.

The mass obtained in the fourth stage is calcined at a temperature of 550° C. for 5 hours in a stream of air.

2-nd scheme:

The number of stages is 12; in each uneven stage there are added 67 ml of solution A, in each even stage there are added 67 ml of solution B. In each stage water is removed from the resulting suspension by way of evaporation and after the final stage the resulting mass is subjected to calcination at a temperature of 550° C. for 5 hours in a stream of air.

Characteristics of the catalysts prepared in the 1-st and 2-nd schemes as well as the results of dehydrogenation processes carried out under the conditions of Example 2 on the catalysts prepared as described hereinbefore are shown in the following Table 1.

TABLE 1

| | Catalyst characteristis | | | | | Dehydrogenation parameters | | Selectivity % | |
|---|---|---|---|---|---|---|---|---|---|
| | Composition, wt. % | | | | | Conversion of n-butane, % | Yield of butadiene, % | relative to butadiene | relative to sum of butylenes and butadiene |
| Scheme | MgO | $TiO_2$ | CoO | $MoO_3$ | $S_{sp.}$, m²/g | | | | |
| I | 65.7 | 20.9 | 4.9 | 8.5 | 21.1 | 29.7 | 14.1 | 47.5 | 49.6 |
| II | 66.1 | 21.8 | 4.2 | 7.9 | 25.7 | 35.1 | 19.6 | 56.0 | 68.4 |

EXAMPLE 7

A catalyst is prepared following the procedure described in the foregoing Example 5, except that after application of the active components the resulting mass prior to calcination is treated with an aqueous solution of ammonia, an amine or aminoalcohol. From the resulting suspension water is removed at a temperature within the range of from 60° to 180° C. and the thus-obtained mass is calcined at a temperature within the range of from 540° to 560° C. for 5 hours in an air atmosphere.

Characteristics of the thus-prepared catalyst as well as the results of the dehydrogenation process performed under the conditions of Example 2 hereinbefore using the catalyst prepared as above are given in Table 2.

EXAMPLE 8

Preparation of a catalyst is carried out following the procedure described in the foregoing Example 6 (2-nd scheme), except that instead of the solution of cobalt nitrate for the preparation of the catalyst use is made of one of the following solutions:

(1) solution of 63.2 g of nickel nitrate in 400 ml of distilled water;

(2) solution of 74.4 g of iron nitrate in 400 ml of distilled water;

(3) solution of 62.4 g of manganese nitrate in 400 ml of distilled water.

The process of dehydrogenation of n-butane is conducted continuously for 1,000 hours. The data are given in Table 4 hereinbelow.

TABLE 2

| No. | Reagent used for the treatment of the mass | Catalyst characteristics: Composition, wt. percent | | | | $S_{sp.},$ $m^2/g$ | Dehydrogenation parameters | | | |
|---|---|---|---|---|---|---|---|---|---|---|
| | | MgO | TiO$_2$ | CoO | MoO$_3$ | | Conversion of n-butane, % | Yield of butadiene, % | Selectivity relative to butadiene | relative to sum of butadiene + butylenes |
| 1. | 25% aqueous solution of ammonia | 66.6 | 22.2 | 3.8 | 7.4 | 23.1 | 16.9 | 8.3 | 49.2 | 65.5 |
| 2. | 20% aqueous solution of monoethanolamine | 65.5 | 21.8 | 4.6 | 8.1 | 26.2 | 25.8 | 12.4 | 48.2 | 64.3 |
| 3. | 20% aqueous solution of triethanolamine | 65.5 | 21.8 | 4.6 | 8.1 | 23.5 | 17.4 | 7.8 | 44.9 | 61.9 |
| 4. | 25% aqueous solution of methylamine | 67.4 | 22.3 | 3.7 | 6.6 | 16.8 | 14.8 | 8.0 | 53.9 | 69.8 |
| 5. | 25% aqueous solution of triethylamine | 66.0 | 21.8 | 4.1 | 8.1 | 13.3 | 18.6 | 6.2 | 33.6 | 52.1 |

In all cases use is made of a solution of 40.0 g of ammonium molybdate in 400 g distilled water.

The dehydrogenation process is conducted under the conditions described in Example 2 hereinbefore. Characteristics of the catalysts and results of the dehydrogenation process are shown in the following Table 3.

Upon addition of oxygen to the starting feed in the stage of dehydrogenation in the amount of 0.09 mol/mol of n-butane under the conditions of the foregoing. Example 1, conversion of n-butane is equal to 40.8%, the yield of butadiene is 26.4% with the selectivity relative thereto of 64.7% and relative to the total of butylenes-butadiene of 73.0%.

EXAMPLE 9

TABLE 3

| | Characteristics of the catalyst Composition, wt. percent | | | | | | | Dehydration parameters | | | |
|---|---|---|---|---|---|---|---|---|---|---|---|
| No. | MgO | TiO$_2$ | NiO | FeO | MoO | MoO$_3$ | $S_{sp},$ $m^2/g$ | Conversion of n-butane, % | Yield of butadiene, % | Selectivity, % relative to butadiene, % | relative sum of butadiene and butylene, % |
| 1 | 49.3 | 16.5 | 13.9 | — | — | 20.3 | 42.1 | 22.4 | 14.3 | 63.8 | 73.3 |
| 2 | 48.2 | 16.1 | — | 12.5 | — | 23.2 | 40.7 | 14.6 | 7.1 | 48.6 | 66.0 |
| 3 | 47.2 | 15.8 | — | — | 14.1 | 22.9 | 63.4 | 43.0 | 3.2 | 7.4 | 13.4 |

TABLE 4

| No. | Dehydrogenation temperature, °C | Space velocity of n-butane supply, hr$^{-1}$ | Inert diluent | Molar ratio of butane to the inert diluent | Dehydration time, minutes | Space velocity of the air supply to regeneration, hr$^{-1}$ | Regeneration time, minutes | Conversion of n-butane, % | Yield of butadiene, % | Selectivity relative to butadiene, % | Selectivity relative to the sum of butylenes and butadienes |
|---|---|---|---|---|---|---|---|---|---|---|---|
| 1 | 592 | 40 | argon | 1:10 | 0.5 | 450 | 0.5 | 42.5 | 27.0 | 63.5 | 75.0 |
| 2 | 590 | 40 | nitrogen | 1:10 | 0.5 | 450 | 0.5 | 34.8 | 24.0 | 69.0 | 84.0 |
| 3 | 590 | 107 | argon | 1:3 | 0.5 | 450 | 1.5 | 36.9 | 18.6 | 50.5 | 68.3 |
| 4 | 590 | 20 | argon | 1:25 | 0.5 | 450 | 0.5 | 36.4 | 26.9 | 74.1 | 86.1 |
| 5 | 625 | 80 | argon | 1:10 | 0.5 | 920 | 0.5 | 27.9 | 19.9 | 71.4 | 83.2 |
| 6 | 550 | 105 | argon | 1:13 | 0.01 | 1350 | 0.01 | 34.5 | 22.5 | 65.2 | 74.3 |
| 7 | 590 | 40 | argon | 1:10 | 2.0 | 450 | 2.0 | 26.6 | 17.0 | 64.0 | 81.0 |
| 8 | 590 | 40 | argon | 1:10 | 5.0 | 450 | 5.0 | 25.4 | 14.7 | 57.9 | 79.0 |
| 9 | 700 | 75 | nitrogen | 1:30 | 1.0 | 1000 | 1.0 | 31.6 | 14.7 | 46.5 | 48.2 |

Preparation of the catalyst is effected following the procedure described in Example 6 hereinbefore (2-nd scheme), except that the carrier employed for the preparation of the catalyst is calcined at a temperature of 1,200° C.; after impregnation and drying the carrier is again calcined at a temperature of 350° C.

The final catalyst has the following composition: CoO 4.8% by weight, MoO$_3$ 9.3% by weight, MgO 64.5% by weight, TiO$_2$ 21.4% by weight.

Specific surface area of the catalyst is 15.0 m$^2$/g.

EXAMPLE 10

The dehydrogenation process is carried out using the catalyst described in the foregoing Example 9. As the starting feed use is made of ethylbenzene. The data obtained are given in the following Table 5.

Upon addition of oxygen to the starting feed in the stage of dehydrogenation in the amount of 0.09 mol/mol of C$_6$H$_{10}$ under the conditions described in Example 3 hereinbefore, conversion of ethylbenzene is equal to 97.4%, the yield of styrene is 85.4% with the selectivity relative thereto of 87.8%.

EXAMPLE 11

The dehydrogenation process is conducted using the catalyst described in Example 9 hereinabove. As the starting feed use is made of ethyltoluene. The process is carried out at a temperature of 560° C., space velocity of the supply of ethyltoluene of 40 hr.$^{-1}$, molar ratio between ethyltoluene and argon equal to 1:9, dehydrogenation duration of 1 minute, space velocity of air supply at the stage of regeneration of 490 hr$^{-1}$, regeneration duration of 1.0 minute. Conversion of ethyltoluene is 81.1%, the yield of vinyltoluene is 70.6% with the selectivity relative thereto of 87.3%.

EXAMPLE 12

The dehydrogenation process is conducted using the catalyst described in the foregoing Example 9.

TABLE 5

| No. | Dehydrogenation temperature, °C. | Space velocity of supply of ethylbenzene, hr$^{-1}$ | Molar ratio of ethylbenzene to argon | Dehydrogenation time, min | Space rate of air supply to regeneration hr$^{-1}$ | Regeneration time, min | Conversion of ethylbenzene, % | Yield of styrene, % | Selectivity relative to styrene, % |
|---|---|---|---|---|---|---|---|---|---|
| 1 | 400 | 40 | 1:9 | 0.5 | 300 | 1.0 | 19.1 | 15.3 | 80.1 |
| 2 | 450 | 45 | 1:9 | 1.0 | 200 | 0.5 | 26.4 | 23.0 | 87.2 |
| 3 | 560 | 40 | 1:9 | 1.0 | 400 | 1.0 | 96.1 | 89.3 | 93.0 |
| 4 | 560 | 40 | 1:9 | 10.0 | 400 | 20.0 | 88.7 | 84.3 | 95.0 |
| 5 | 600 | 49 | 1:9 | 1.0 | 490 | 1.0 | 82.5 | 70.0 | 84.9 |

As the starting feed use is made of iso-pentane with a purity of 98% by weight. The process is conducted at a temperature of 550° C., space velocity of iso-pentane supply of 95 hr$^{-1}$, molar ratio between iso-pentane and argon equal to 1:13, dehydrogenation duration of 0.5 minute, space velocity of the air supply of 1,350 hr$^{-1}$ at the stage of regeneration, duration of the regeneration is 0.5 minute. Conversion of iso-pentane is 28.9%, yield of isoprene is 4.2% with the selectivity relative thereto of 14.5% and relative to the total of isoamylene-isoprene of 22.5%.

EXAMPLE 13

The dehydrogenation process is conducted using the catalyst described in Example 9 hereinbefore. As the starting feed use is made of an isopentane-isoamylene fraction having the following composition, percent by weight: 2-methylbutene-1 1.56; 2-methylbutene-2 49.29; 2-methylbutene-3 30.35; isopentane 8.28; n-pentane 4.00, n-pentenes 3.92; isoprene 2.60.

The process is conducted at a temperature of 545° C. space rate of the feed supply of 41 hr$^{-1}$, molar ratio of $\Sigma i$-C$_5$ to steam equal to 1:7, dehydrogenation duration of 0.5 minute, space velocity of the air supply in the regeneration stage of 280 hr$^{-1}$, regeneration time of 0.5 minute. Conversion of the isopentane-isoamylene fraction is 59.4%, the yield of isoprene is 41.4% with the selectivity relative thereto of 69.7%.

EXAMPLE 14

Preparation of the catalyst is performed following the procedure described in the foregoing Example 6 (2-nd scheme). The carrier employed for the catalyst preparation consists of 50% by weight of magnesia and 50% by weight of titania; the catalyst carrier is calcined at a temperature of 1,400° C.

A catalyst is thus obtained with the following composition: MgO 43.2% by weight, TiO$_2$ 43.1% by weight, CoO 4.7% by weight, MoO$_3$ 9.0% by weight.

Specific surface area of the catalyst is 13.9 m$^2$/g.

The dehydrogenation process using the resulting catalyst is conducted under the conditions of Example 2 hereinbefore.

Conversion of n-butane is 15.9%, the yield of butadiene is 6.5% with the selectivity relative to butadiene of 40.5% and relative to the total of butylenes-butadiene of 64.7%.

EXAMPLE 15

Preparation of the catalyst is effected following the procedure described in Example 5 hereinbefore, except that the carrier employed for the catalyst preparation consists of 95% by weight of magnesia and 5% by weight of alumina and the removal of water from the suspension is performed under vacuum at a temperature within the range of from 60° to 70° C. A catalyst is thus prepared which has the following composition: MgO 78.8% by weight, Al$_2$O$_3$ 4.1% by weight, CoO 6.2% by weight, MoO$_3$ 10.9% by weight.

Specific surface area of the catalyst is 17.6 m$^2$/g.

Dehydrogenation process with use of the resulting catalyst is carried out under the conditions of the foregoing Example 2.

Conversion of n-butane is 24.3%, the yield of butadiene is 5.6% with the selectivity relative thereto of 23.1% and relative to the total of butylenes-butadiene of 29.7%.

EXAMPLE 16

As a carrier for the preparation of a catalyst use is made of a porous crystalline silica (fraction with the particle size of 0.1 to 0.3 mm) calcined at 1100° C., modified with alumina. The modification of silica is conducted by impregnation thereof with an aqueous solution of magnesium nitrate, followed by the removal of excess solution, drying at a temperature within the range of from 110° to 120° C. and calcination at a temperature of from 370° to 400° C. The content of magnesia on silica is varied by appropriately adjusting concentrations of the impregnating solution. The resulting carriers have the following characteristics depending on the content of magnesia:

| No. | Magnesia content as calculated for the carrier, wt. % | Specific surface area, m$^2$/g | Bulk weight, g/cm$^3$ |
|---|---|---|---|
| 1 | 1.0 | 0.6 | 0.80 |
| 2 | 12.8 | 7.6 | 0.92 |
| 3 | 20.0 | 8.1 | 0.94 |

To prepare the catalyst, a solution of 24.0 g ammonium molybdate in 500 ml of distilled water is mixed with 100 g of the carrier. From the resulting suspension water is removed by evaporation at a temperature within the range of from 80° to 150° C. Then the resulting mass is mixed with a solution of 39.5 g of cobalt nitrate in 500 ml of distilled water with 100 g of the carrier. From the resulting suspension water is removed by evaporation at a temperature of from 80° to 120° C. and the thus-produced mass is calcined at a temperature of from 540° to 560° C. The resulting catalysts have the following characteristics depending on the starting carrier employed:

| No. | Content of the active components as calculated for the catalyst, wt. % | | Catalyst specific surface area, $m^2/g$ | Catalyst bulk weight, $g/cm^3$ |
|---|---|---|---|---|
| | CoO | $MoO_3$ | | |
| 1 | 7.6 | 8.8 | 1.3 | 0.9 |
| 2 | 4.6 | 8.7 | 7.6 | 1.0 |
| 3 | 5.8 | 5.8 | 8.2 | 1.1 |

The process of dehydrogenation is carried out in a reactor similar to that described in the foregoing Example 1. Using the catalyst No. 1 (see the above Table), through the reactor at the temperature of 570° C. i-pentane is passed at the space rate of 105 $hr^{-1}$ at the molar ratio of i-pentane to helium of 1:13. The duration of i-pentane supply is 1.0 minute. Space velocity of the air supply in the regeneration stage is 1,350 $hr^{-1}$ with the supply duration of 1.0 minute. The total process time is 5 hours.

Conversion of i-pentane is 7.7%, the yield of isoprene is 3.6% with a selectivity relative thereto of 46.8% and relative to the sum of isoamylenes-isoprene of 58.6%.

Using the catalyst No. 2, through a reactor at the temperature of 550° C. n-butane is passed at a space velocity of 80 $hr^{-1}$ at a molar ratio between n-butane and the diluent of 1:15. As the diluent use is made of a mixture of 80% by weight of steam and 20% by weight of nitrogen. The duration of n-butane supply is 1 sec. Space velocity of the air supply is 1,200 $hr^{-1}$ with the supply duration of 0.5 minute. The total duration of the process is 0.5 hour.

Conversion of n-butane is 17.8%, the yield of butadiene is 8.7% with the selectivity relative thereto of 48.9% and relative to the total of butylenes-butadiene of 54.3%.

Using the catalyst No. 3, through a reactor at the temperature of 560° C. with a space velocity of 90 $hr^{-1}$ a mixture of hydrocarbons is passed consisting of 21.1% by weight of diethyltoluene, 65.6% by weight of ethyltoluene, 11.9% by weight of ethylbenzene and 1.4% by weight of toluene. The molar ratio between the hydrocarbon feed and nitrogen is equal to 1:9. Duration of the feed supply is 1 minute. Space velocity of the air supply in the stage of regeneration is 900 $hr^{-1}$, supply duration is 1 minute. The total duration of the process is one hour.

Conversion of ethyltoluene is 53.2%, the yield of vinyltoluene is 42.6% with the selectivity relative thereto of 80.1%. The yield of divinyltoluene is 2.1%, the yield of vinylethyltoluene is 1.6%, the yield of styrene is 12.6% as calculated for the total starting hydrocarbon feed.

What is claimed is:

1. A process for producing unsaturated hydrocarbons comprising contacting compounds selected from the group consisting of paraffin, monoolefin and alkylaromatic hydrocarbons at a temperature within the range of from 400° to 700° C. in the presence of an inert component selected from the group consisting of an inert gas and steam, and in the presence of oxygen in an amount up to 0.1 mole per mole of the hydrocarbon feed, with a catalyst consisting essentially of oxides selected from the group consisting of cobalt, nickel, iron and manganese deposited on a carrier in an amount of from 3.7 to 15% by weight of the catalyst; said catalyst also including an oxide of molybdenum in an amount of from 5 to 35% by weight of the catalyst, also deposited on the carrier; said carrier being selected from the group consisting of granulated porous crystalline silica modified with magnesia in an amount of 1 to 20% by weight of the carrier, granulated magnesium-titanium oxides consisting of 50 to 95% by weight of MgO and 50 to 5% by weight of $TiO_2$ and granulated magnesium-aluminum oxides consisting of 70 to 95% by weight of MgO and 5 to 30% by weight of $Al_2O_3$; passing an oxygen-containing gas through the spent catalyst at a temperature within the range of from 400° to 700° C. to restore catalytic activity of the catalyst.

2. A process for preparing a catalyst consisting essentially of oxides selected from the group consisting of cobalt, nickel, iron and manganese deposited on a carrier in an amount of from 3.7 to 15% by weight of the catalyst; said catalyst also including an oxide of molybdenum in an amount from 5 to 35% by weight of the catalyst, also deposited on the carrier; said carrier being selected from the group consisting of granulated porous crystalline silica modified with magnesia in an amount of 1 to 20% by weight of the carrier, granulated magnesium-titanium oxides consisting of 50 to 95% by weight of MgO and 50 to 5% by weight of $TiO_2$, and granulated magnesium-aluminum oxides consisting of 70 to 95% by weight of MgO and 5 to 30% by weight of $Al_2O_3$; said catalyst being prepared by first impregnating the carrier with an aqueous solution of ammonium molybdate to obtain a suspension, wherefrom water is removed by evaporation, and the carrier is subjected to a second impregnation with an aqueous solution of a metal nitrate selected from the group consisting of cobalt, nickel, iron and manganese, and calcining the resulting mass at a temperature within the range of from 350° to 700° C. in a medium selected from the group consisting of an inert medium and an oxidizing medium.

3. The catalyst formed by the process of claim 2.

4. A process as claimed in claim 2, wherein said impregnation with aqueous solutions of salts and removal of water by evaporation is repeated for 3 to 12 times.

5. A process as claimed in claim 2, wherein the removal of water from the suspension by evaporation is effected under vacuum.

6. A process as claimed in claim 2, wherein calcination of the resulting mass is effected in a fluidized bed.

7. A process as claimed in claim 2, wherein the resulting carrier mass, impregnated with aqueous solutions of ammonium molybdate and a nitric salt and dried, is treated, prior to calcination, with an aqueous solution of a nitrogen-containing compound selected from the group consisting of ammonia, amines and aminoalcohols, followed by the removal of water by evaporation.

8. A process as claimed in claim 7, wherein the aqueous amine solutions are selected from the group consisting of methylamine and triethylamine.

9. A process as claimed in claim 7, wherein the aqueous aminoalcohol solutions are selected from the group consisting of monoethanolamine and triethanolamine.

* * * * *